US009823101B2

(12) United States Patent
Freifeld et al.

(10) Patent No.: US 9,823,101 B2
(45) Date of Patent: Nov. 21, 2017

(54) AUTOMATED STENT INSPECTION SYSTEM

(71) Applicant: Electro Scientific Industries, Inc., Portland, OR (US)

(72) Inventors: Daniel Freifeld, Napa, CA (US); John Roberts, Orinda, CA (US); John B. Burnett, Vacaville, CA (US); George Linscott, El Dorado, CA (US)

(73) Assignee: Electro Scientific Industries, Inc., Portland, OR (US)

( * ) Notice: Subject to any disclaimer, the term of this patent is extended or adjusted under 35 U.S.C. 154(b) by 541 days.

(21) Appl. No.: 13/915,463

(22) Filed: Jun. 11, 2013

(65) Prior Publication Data

US 2013/0329036 A1 Dec. 12, 2013

Related U.S. Application Data

(60) Provisional application No. 61/658,448, filed on Jun. 12, 2012.

(51) Int. Cl.
*G01D 21/00* (2006.01)
*H04N 7/18* (2006.01)
*G01N 21/952* (2006.01)
*A61F 2/82* (2013.01)

(52) U.S. Cl.
CPC ........... *G01D 21/00* (2013.01); *G01N 21/952* (2013.01); *H04N 7/18* (2013.01); *A61F 2/82* (2013.01); *A61F 2240/008* (2013.01)

(58) Field of Classification Search
CPC .......... G01D 21/00; H04N 7/18; G01N 2/952; A61F 2/82; A61F 2240/008
See application file for complete search history.

(56) References Cited

U.S. PATENT DOCUMENTS

| | | | |
|---|---|---|---|
| 6,091,872 A | * | 7/2000 | Katoot ............ B29D 11/00721 385/115 |
| 6,879,403 B2 | | 4/2005 | Freifeld |
| 6,957,152 B1 | | 10/2005 | Esbeck |
| 7,020,324 B2 | | 3/2006 | Freifeld |
| 7,619,646 B2 | | 11/2009 | Freifeld et al. |
| 2004/0013792 A1 | | 1/2004 | Epstein et al. |
| 2006/0224421 A1 | | 10/2006 | St. Ores et al. |
| 2007/0082120 A1 | | 4/2007 | Diaz et al. |
| 2008/0067728 A1 | | 3/2008 | Plans et al. |
| 2008/0311281 A1 | | 12/2008 | Andreacchi et al. |

(Continued)

OTHER PUBLICATIONS

Visicon Technologies, Inc.; PCT/US13/45315; International Search Report; Mailed Feb. 18, 2014.

(Continued)

*Primary Examiner* — Gims Philippe
*Assistant Examiner* — Jill Sechser

(57) ABSTRACT

A method for the rapid optical inspection of stents is described wherein a stent is mounted on a mandrel with optical properties suitable for machine vision inspection of the stent is conveyed to a first inspection station containing a camera and illumination light source. A driving member securely contacts the mandrel and the stent is rotated in view of the inspection camera. The stent is then transferred to a second location for further operations. A unique identification tag is associated with each mandrel and tracks the location of the stent through the inspection process.

21 Claims, 6 Drawing Sheets

(56) References Cited

U.S. PATENT DOCUMENTS

| | | |
|---|---|---|
| 2010/0014747 A1 | 1/2010 | Freifeld |
| 2010/0053317 A1* | 3/2010 | Freifeld ............... G01N 21/954 |
| | | 348/85 |
| 2010/0245055 A1 | 9/2010 | Freeman et al. |
| 2010/0309307 A1 | 12/2010 | Jin |
| 2011/0007147 A1* | 1/2011 | Cameron .................. A61F 2/91 |
| | | 348/92 |

OTHER PUBLICATIONS

Extended European Search Report in European Patent Application No. 13804552.1, mailed Jan. 11, 2016.
Written Opinion issued Feb. 18, 2014 concerning PCT Application No. PCT/US2013/045315, which corresponds with the subject U.S. Appl. No. 13/915,463. 6 pages.
European Search Report Issued Dec. 23, 2015 concerning European Patent Application No. EP13804552, which corresponds with the subject U.S. Appl. No. 13/915,463. 4 pages.

* cited by examiner

AUTOMATED STENT INSPECTION SYSTEM

CROSS REFERENCE TO RELATED APPLICATIONS

This patent application claims priority to the filing date of U.S. Provisional Patent Application Ser. No. 61/658,448 that was filed on Jun. 12, 2012 and is titled "Automated Stent Inspection System". The disclosure of U.S. Provisional Patent Application Ser. No. 61/658,448 is incorporated by reference in its entirety herein.

U.S. GOVERNMENT RIGHTS

N.A.

BACKGROUND OF THE INVENTION

Field of the Invention

This invention relates to inspection systems for small, at least partially rotationally symmetric, cylindrical objects, such as stents. More particularly, a mandrel is configured for the inspection and identification of the objects.

Description of the Related Art

Current automated inspection systems such as the FineScan® and Sierra™ systems from Visicon Technologies Inc., (Napa, Calif.) are well known in the stent industry for providing machine assisted dimensional and visual defect inspection of stents. These systems rely on a translucent mandrel that provides a bright contrast background as the stent is rotated in front of a line scan camera to build up a line-by-line unrolled image of the stent. While these systems provide fast and reliable inspection, physically loading the stents on the mandrels is time consuming and requires a high degree of manual dexterity as the mandrels are not easily mounted and dismounted from the system on their own. Further, these mandrels are somewhat expensive and fragile. So an automatic method of loading and unloading such an inspection machine would be desired.

Systems for inspecting stents and measuring dimensions of stents are disclosed in U.S. Pat. No. 6,879,403, "Three Dimensional Scanning Camera" by Freifeld, U.S. Pat. No. 7,020,324, "Precision measurement of Tube Wall Thickness," by Freifeld and U.S. Pat. No. 7,619,646, "System and Method to Illuminate the Inside Diameter of a Stent," by Freifeld et al. All three of U.S. Pat. Nos. 6,879,403; 7,020,324 and 7,619,646 are incorporated by reference in their entireties herein.

It is also important to relate the inspection results for a given stent to its manufacturing conditions such as which location in a polishing machine it occupied. Currently, manual systems of tagging the stent with information related to prior manufacturing steps are employed so any automated handling system must also provide a means to provide single part traceability. As with any manual operation in a medical device production the potential exists for a human to choose the wrong mandrel for the given inspection. If would be preferred if this was failsafe in an automatic handling approach.

There remains a need for systems and components for the inspection and identification of stents and other cylindrical objects that does not have the limitations of the prior art methods.

BRIEF SUMMARY OF THE INVENTION

The details of one or more embodiments of the invention are set forth in the accompanying drawings and the description below. Other features, objects and advantages of the invention will be apparent from the description and drawings, and from the claims.

Disclosed herein is a system to provide a system to load and unload a machine based stent inspection device with greatly reduced or no human labor. A further goal is to prevent scratching of the inner diameter of the stent. A feature of the system is to associate each mandrel with a code containing or referring to a data record that allows verification that the correct mandrel for a given inspection recipe is used and also to store performance and historical data related to the mandrel so that for example the correct light intensity might be recalled for a given mandrel and in another example an alert can be provided should the mandrel require maintenance. This data record can also be used to associate inspection results to the specific production parameters used for that given part. A goal of the system is to simplify the weighing of a stent.

BRIEF DESCRIPTION OF THE DRAWINGS

Like reference numbers and designations in the various drawings indicate like elements.

DETAILED DESCRIPTION

Figure 1:
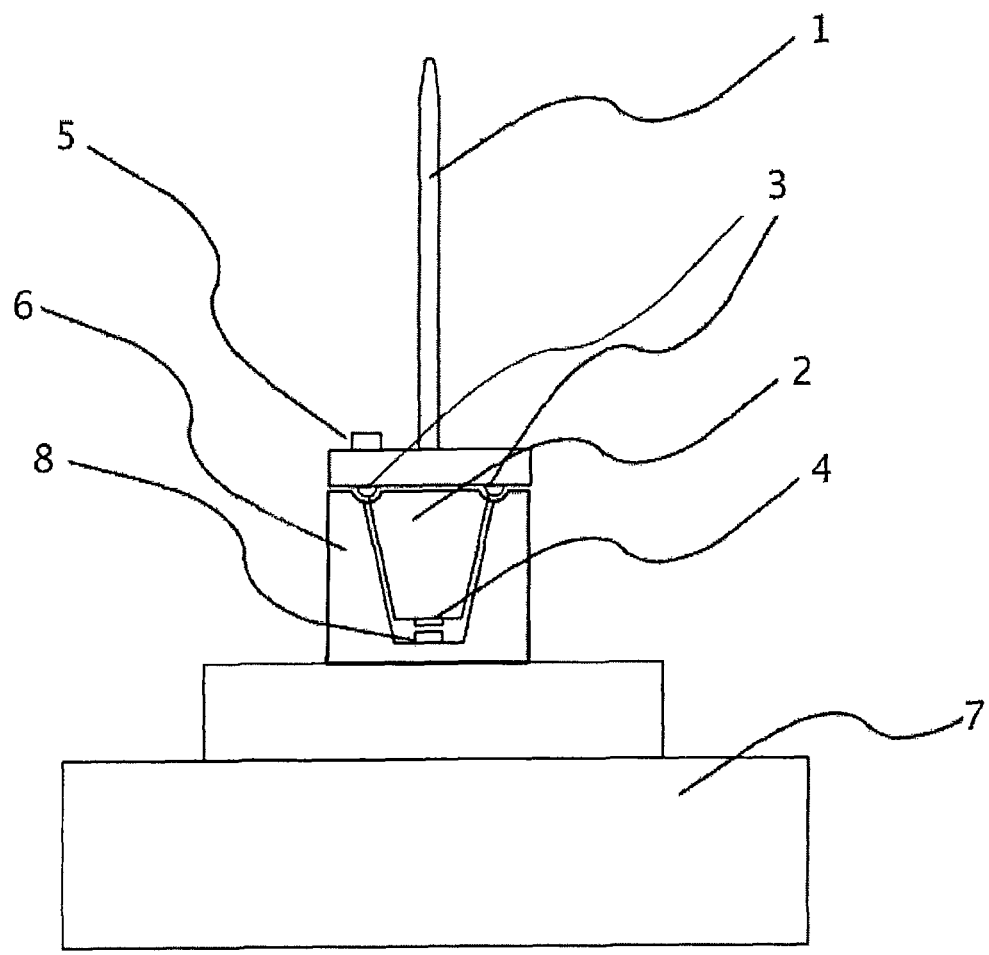
FIG. 1 illustrates an automated inspection system in accordance with a first embodiment disclosed herein.

The inspection system described herein is particularly suited for the inspection of cylindrical parts having at least partial rotational symmetry. More particularly for the inspection of medical implant components, such as stents. A stent is mounted on a mandrel suitable for optical inspection. The mandrel includes a rod that is sized to receive the stent so that the stent will not slip or fall off. The rod is formed from a stiff material to remain straight while rotating in view of a camera performing an optical inspection. The mandrel rod has a uniform appearance and provides a proper background for optical inspection. The mandrel rod material is sufficiently smooth to avoid scratching interior surfaces of the stent. Materials of choice for the mandrel rod include, without limitation, ceramic, sapphire, glass, and engineered plastics such as Radel-R® plastic, a high temperature polyphenylsulfone thermoplastic, available from Curbell Plastics, Phoeniz, Ariz.

The rod can be optically transmissive or reflective depending on the inspection approach. Alternatively the rod is coated with Teflon® (polytetrafluoroetylene, trademark of DuPont, Wilmington, Del.) to prevent scratching. With a camera looking down on a horizontal rod, a transmissive rod will be illuminated from below; while a reflective rod would be illuminated from above.

At one end of the mandrel is a base suitable for mounting and dismounting in a receiving fixture to hold the mandrel in proper position within the optical inspection system. In one preferred embodiment the mandrel base has mechanical registration to the straightness of the rod such that when mounted on the inspection system this registration is precisely preserved through the receiving fixture accepting the base and thus allowing the rod to rotate precisely orthogonal to the optical axis of the inspection system.

The mandrel base and mechanical receiving fixture are intended to provide quick and easy means of attachment and removal. A pneumatic or magnetic chucking mechanism accommodates this requirement. The base can also be used to transfer the mandrel from a queuing station to one or more inspection stations by mechanical means.

The mandrel may also contain an identification code referencing data pertinent to the historical and proper use of the given mandrel as well as any inspection results or prior manufacturing data. The identification code integral to the mandrel can be a radio frequency identification (RFID) tag, 2-dimensional barcode or other known method of identification. In one preferred embodiment the identification code will refer to a data record resident on a computer. Alternatively this data code could be reconfigurable and contain the data directly.

This identification code can be used to track single mandrels and the associated stents through the inspection process and capture and preserve traceability of the specific production parameters associated with that given stent. When a stent is introduced to a given mandrel, a data file is created relating the known manufacturing information on that given stent to the unique identification code associated with the given mandrel.

The optical inspection system is capable of sensing the presence of the mandrel using a proximity, optical or other suitable sensor. When the mandrel is introduced to a camera station within the inspection system it will then read the data code. The inspection system can then use the code information in a variety of ways. The inspection system can determine which inspection protocol to run. Alternatively, the inspection system can determine if a user has indeed chosen the correct mandrel for the inspection recipe already selected. The inspection system can also determine certain critical mandrel specific parameters to use for a given protocol, such as required light intensity for a particular mandrel and software correction for a lack of mechanical straightness of that mandrel.

As the quality of the production process can in part be monitored through control of stent weight, the identification code can also contain a tare weight of the mandrel without a stent. When the stent is mounted on the mandrel it can be moved to a balance and weighed without removal from the mandrel.

In one alternative embodiment, a flexible coupling is interposed between the rod and the motor. The precision alignment of the rotating rod to the optical axis of the lens is maintained by a mechanical alignment means in direct contact with the rod.

In another alternative embodiment, the rod is separate from the base and the data code is affixed directly to the rod. Here the rod will be gripped directly and rotated under the inspection camera. Precise mechanical registration of the rod to the optical axis is obtained by either a receiving collet that is rigidly attached to a motor with high precision of rotation and alignment or by a flexible coupling between the rod and the motor with a mechanical guiding fixture that captures the rod in the correct alignment to the optical axis. While there are many ways to rotate a cylindrical object precisely, a preferred embodiment is two precision V's that the mandrel is held against with a vacuum or mechanical attachment.

The data code on the rod or mandrel can also be helpful after the inspection. Often a complex, expensive to produce, part like a stent is manufactured in an environment that is not a perfect clean room. Sometimes a small piece of dust might appear to an inspection system as a defect. Often human operators can discern the difference between a true defect and a "nuisance" alarm such as dust by careful review of multiple images taken of the area under question—the possible defect.

In a highly automated parts handling situation, it is disadvantageous for the automation system to stop processing parts and wait for a human operator to make a decision regarding the pass/fail adjudication of a particular possible defect. In this case a separate defect review station is preferred. Here an operator can bring a tray of parts that have been inspected by an automated inspection system. This tray of parts can have a bar code or RFID or other similar identification method, with each location in the tray related to a particular part. A data record is maintained on a separate computer or manufacturing information system (MIS) that has the inspection records and stored images for the given part.

The operator is shown images of the possible defects of each part in the tray that were taken and stored by the automatic vision system. The operator is asked to determine if a possible defect is truly bad and reject the part or is just a nuisance, like dust, and can pass the part. If the stored images are not clear enough, the operator might take the part from the tray to inspect it manually on a microscope. A camera can be placed above the tray to make sure the operator takes and replaces the correct parts appropriately. Often there will be a reject bin for bad parts and the camera would then verify the correct part was not put back in the tray. If a robot or other automated means is used to handle the parts, a camera might not be needed.

If the parts come to the defect review station on a mandrel that contains a data code and rotational index, the mandrel can be loaded on an X,Y,Z,R motion control platform and the system can drive to the exact possible defect location as stored in the inspection data record. This will save the operator time in re-inspecting those parts that have possible defects too difficult to adjudicate based solely on the saved images.

FIG. 1 illustrates a first embodiment of a stent inspection system. A mandrel includes a rod 1 mounted on a base 2. Alignment balls 3, typically there are three alignment balls 3 although two are visible in FIG. 1, preserve the alignment of the rod 1 relative to a receiver 6 when placed in the receiver 6. The rod 1, base 2 and receiving fixture 6 are fixedly connected one to another such that the three components remain in rotational alignment. A first magnet 4 is placed at the bottom of the base 2 to secure that base 2 in the receiver by attraction to a complimentary magnet 8 affixed to the receiver 6. An RFID tag 5 is mounted at the top of the base 2. The receiver is attached to a motorized rotary stage 7.

Figure 2:
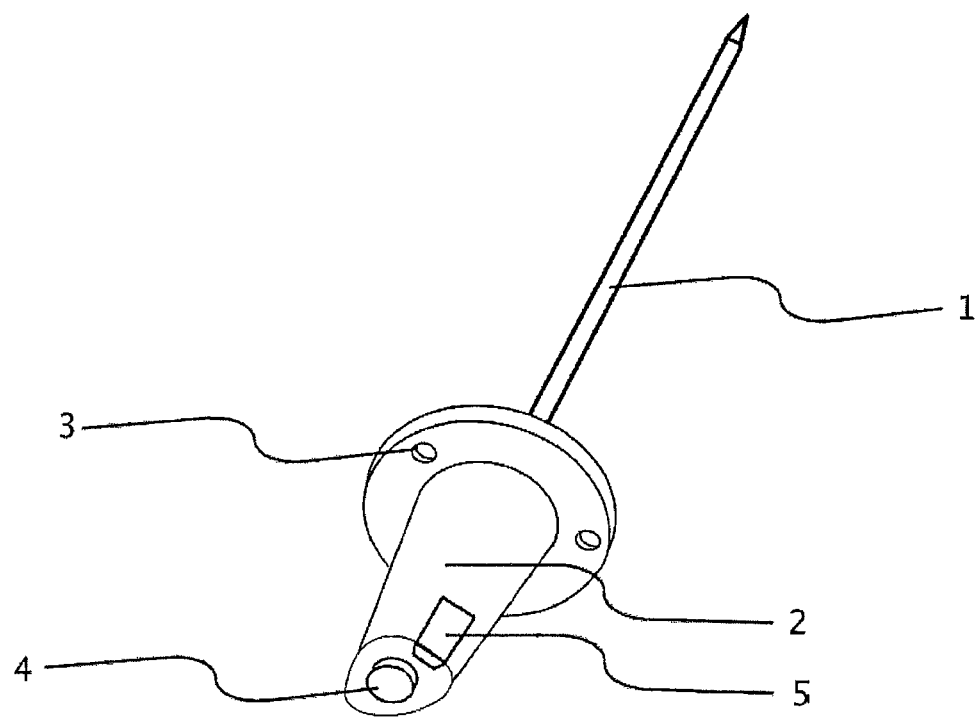
FIG. 2 illustrates an alternative base for use with the inspection system of FIG. 1.

FIG. 2 illustrates and alternative base 2 that has an asymmetric form so that its orientation is uniquely registered in rotation to a receiver. The alternative base 2 has an indicating feature that is not rotationally symmetric and can be used to register the rotational orientation of the rod 1 attached to the base 2 component of the mandrel to a home position of an encoder when aligned to the mechanical receiving fixture in response to the indicating feature. In this embodiment, the RFID tag 5 is positioned at the bottom of the base 2. If a sensor for the RFID tag 5 is positioned within the receiver, the receiver can act as an electromagnetic shield and the sensor will only detect the given mandrel that is loaded into the receiver.

FIGS. 3A-3D illustrate alignment fixtures 10 for use with the automated inspection system. In all embodiments, a stent 20 is mounted onto the rod 1. The various embodiments present different approaches to using the alignment fixture 10 to assure the rod 1 rotates with high precision and negligible run-out. By use of the alignment fixture 10, high precision alignment from the rod 1 to the base 2 to a rotational motor 12 is not required.

Figure 3:
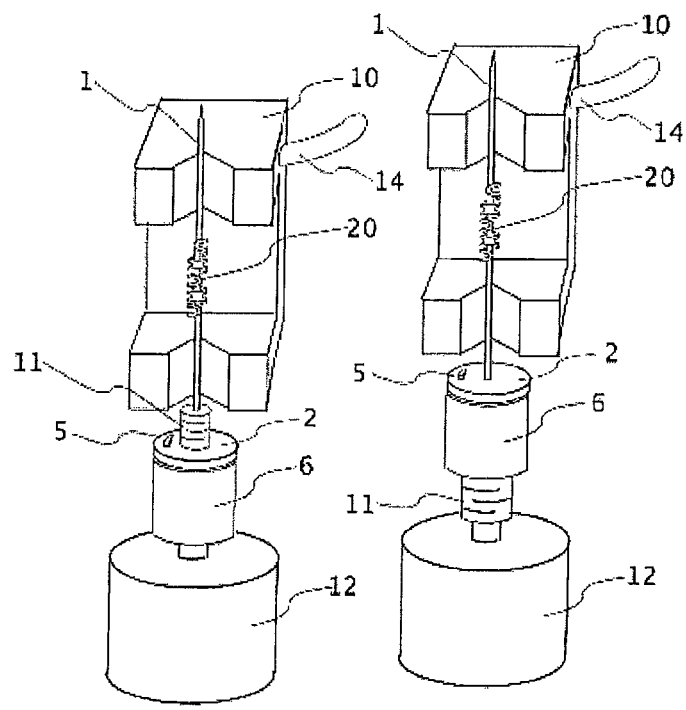
FIG. 3A illustrates a first alignment fixture for use with the automated inspection system of FIG. 1.
FIG. 3B illustrates a second alignment fixture for use with the automated inspection system of FIG. 1.
FIG. 3C illustrates a third alignment fixture for use with the automated inspection system of FIG. 1.
FIG. 3D illustrates a fourth alignment fixture for use with the automated inspection system of FIG. 1.
Figure 3:
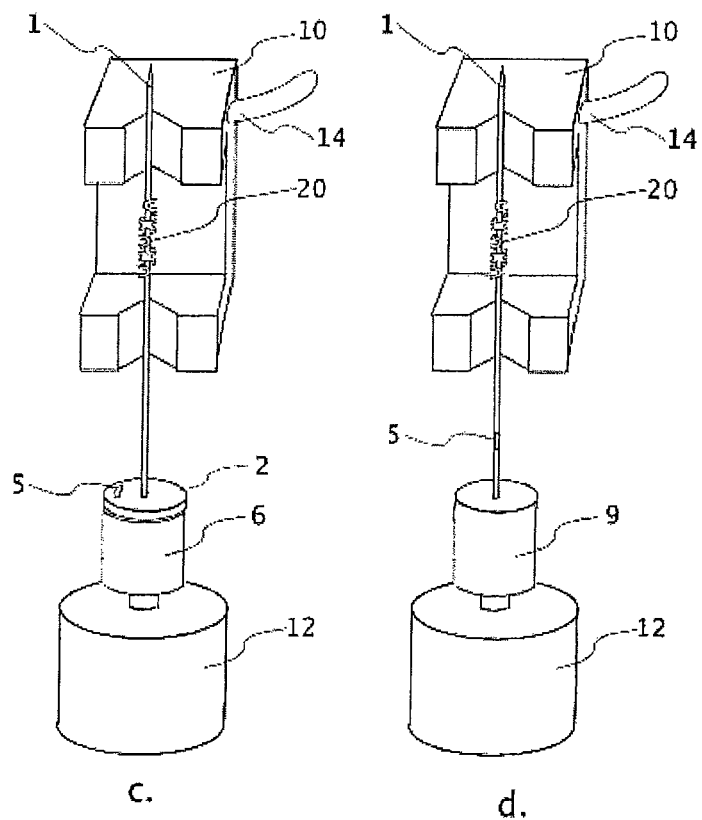

In the embodiments illustrated in FIGS. 3A and 3B, a flexible coupling 11 is used to isolate the alignment of the rod 1 in the alignment fixture 10. In the embodiment illustrated in FIG. 3A, the flexible coupling 11 is located between the rod 1 and the mandrel base 2. In the embodiment illustrated in FIG. 3B, the flexible coupling 11 is located between the receiver 6 and the rotational motor 12. The flexible coupling 11 between the motor and the receiving fixture allows constraint of the rod by at least one fixed mechanical guide to constrain rotation of the rod about a center axis precisely perpendicular to the optical axis of the lens.

In the embodiment illustrated in FIG. 3C, an extra long rod 1 is used so the flexibility of the rod 1 itself is used to accommodate any misalignment between the alignment fixture 10 and the other components. In the embodiment illustrated in FIG. 3D, the rod 1 includes the data code 5 mounted directly on the rod 1 and a rubber cylinder 9 with a hole in the center accommodates the rod 1. The length of the rod 1 and the compliance of the rubber cylinder 9 allow for misalignment between the rotational motor 12 and the rod 1.

In all four embodiments, a vacuum is drawn through a tube 14 from an opening behind the rod 1 within the alignment fixture 10 to keep the rod in contact with a precision V-block.

The alignment fixtures are useful with an optical inspection system. The optical inspection system includes a lens for imaging an at least partially rotationally symmetric part under inspection. A lens images the part under inspection and an electronic camera captures images projected by the lens. A mandrel to support the part under inspection includes a rod of diameter to accommodate mounting of the part and a mechanical base attached to the rod. A rotating motor driven mechanical receiving fixture is responsively configured to receive the mechanical base of the mandrel where rotation of the rod is about a center axis perpendicular to an optical axis of the lens. An encoder responsive to the rotating motor triggers image capture of the electronic camera based on position of the part in view of the camera. The mandrel further has a data code referencing information pertinent to the inspection and processing of the part under inspection.

Figure 4:
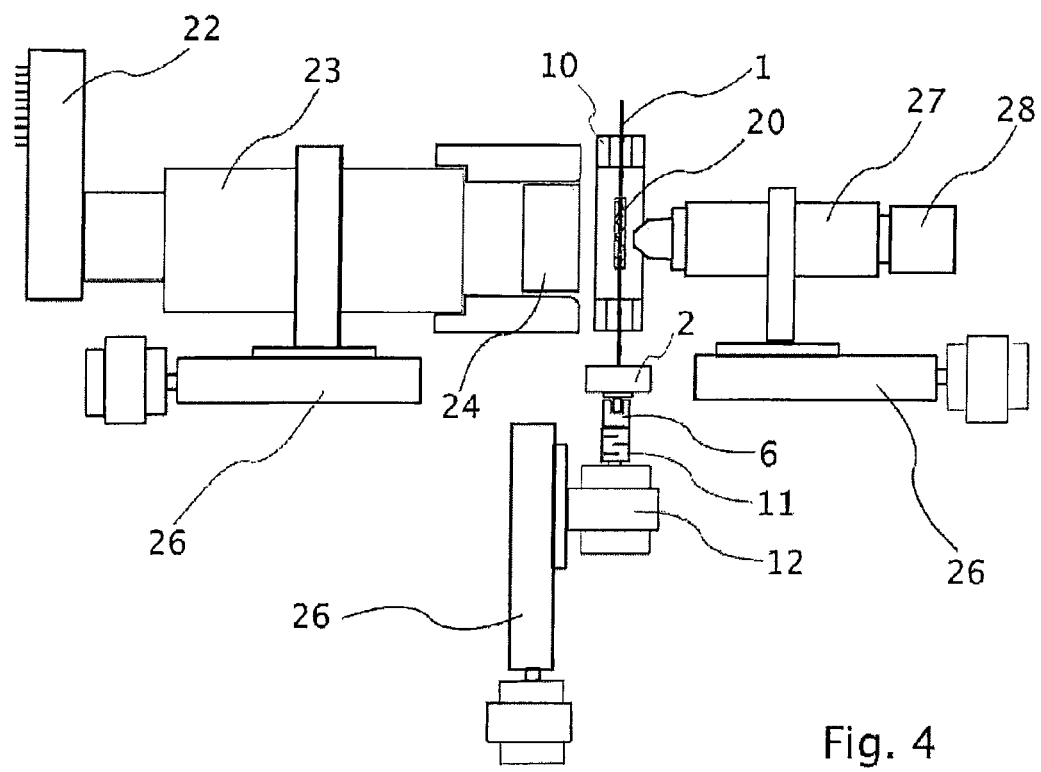
FIG. 4 shows a camera system included with the automated inspection system of FIG. 1.

FIG. 4 illustrates one such optical inspection system. A stent 20 is mounted on a rod 1 and held in precise alignment by an alignment fixture 10. The stent 20 is imaged by a line scan camera 22 such as the Piranha HS from Teledyne Dalsa Inc. (Waterloo, Canada) using a large format lens 23 and illuminated by an on-axis light source 24. The line scan camera includes a line sensor positioned perpendicular to an optical axis of the large format lens 23 and parallel to a center axis of the rod 1. The large format lens 23 is mounted on a motorized slide 26 to control focus. For defect classification a higher magnification lens 27 such as the Archrovoid Video Microscope from Infinity Photo-Optical (Boulder, Colo.) is used. A video camera 28 such as the A600 available from Basler GmbH (Ahrensburg, Germany) is mounted along with the higher magnification lens 27 on a second motorized slide 26' for positioning and is used to take a closer look at possible defects the system locates with the line scan camera 22.

The rod (1) is mounted in base (2) mounted in a receiving fixture (6) that is connected with a flexible coupler (11) to a rotational motor (12), which is moved by a third motorized slide (26) to enable the stent to be repositioned in the field of view of the lenses.

Figure 5:
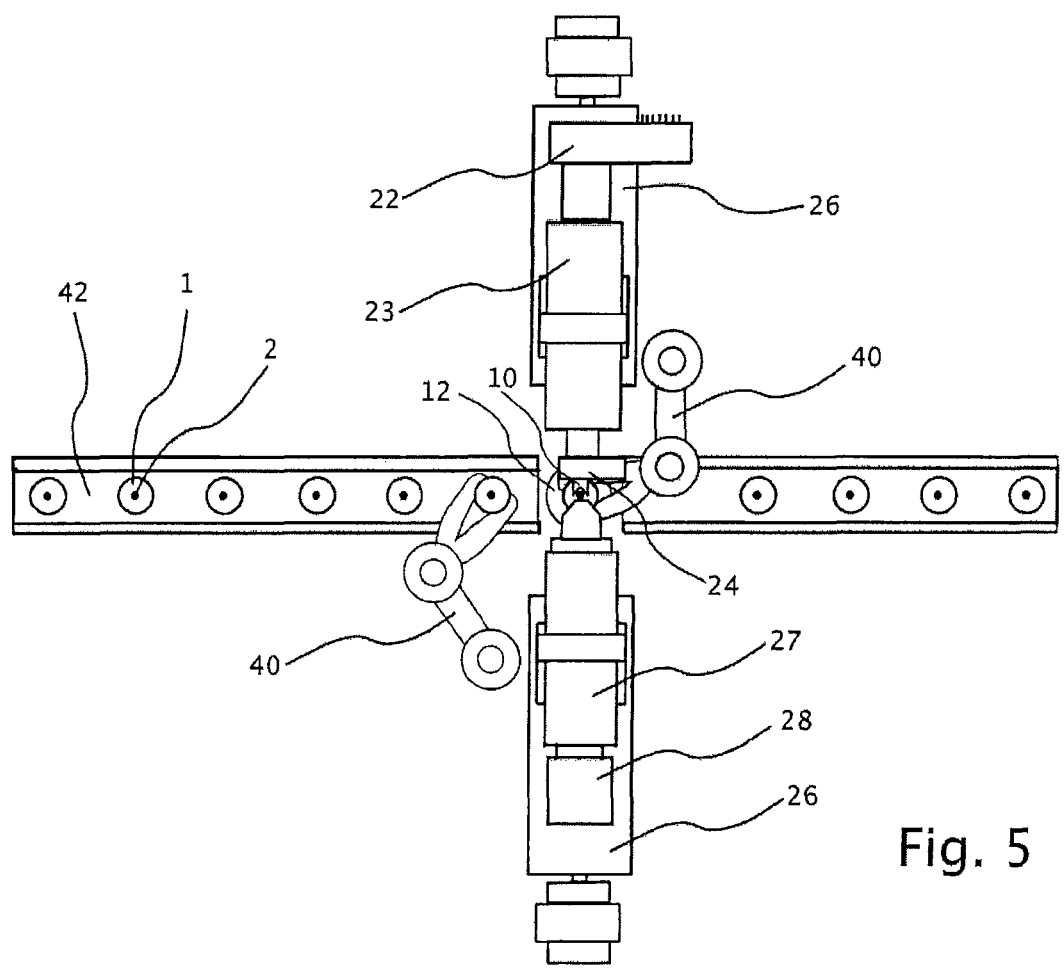
FIG. 5 shows a conveyor moving mandrels to and from an inspection station.

FIG. 5 shows a conveyor (42) moving mandrels comprised of a rod (1) and a base (2) to and from an inspection station. When the mandrel is adjacent to the inspection station a robotic arm (40) moves the mandrel into position registered by an alignment fixture (10). Once in position, a motor (12) is activated to rotate the mandrel. A line camera (22) then takes an image through a lens (23) of the stent on the mandrel as it is rotated by motor (12). A second camera with an area sensor is available to take a higher resolution image of potential defects through the lens (27). A stage (26) is used to position and focus both lens assemblies.

Figure 6:
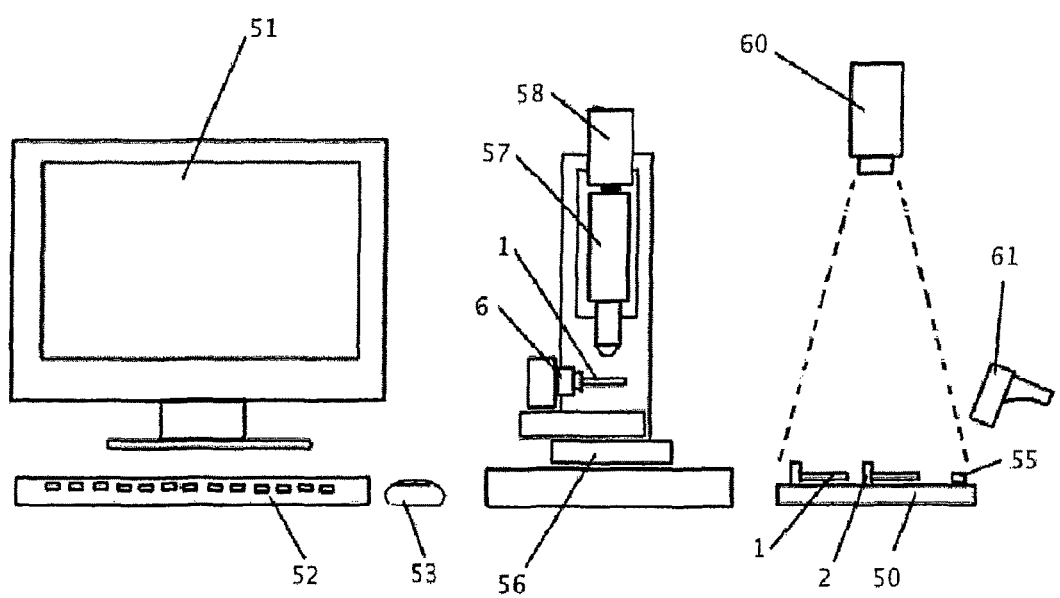
FIG. 6 shows a defect review station configured to hold a set of parts.

FIG. 6 shows a defect review station comprised of a tray (50) configured to hold a set of parts on mandrels composed of a rod (1) and base (2). An alternative tray could hold just the raw parts, but if they are on a mandrel that has a rotational indicator the mandrel could be then set under a video microscope (57) with camera (58) that is configured to focus on the part placed on a rod (1). A receiver (6) allows the proper orientation so the part can be positioned by an X, Y, Z, R motion system (56) to see a live image of the specific defect found by a prior automated inspection step on computer 51. The operator reviews either a stored image or a live image or both and makes a determination regarding whether the possible defect is severe enough to reject the part. Once the operator makes this determination she enters this result as well as the defect classification as to cause with the mouse (53) or the keyboard (52). If the part is rejected it will not be placed back in the same position on the tray.

A camera 60 continually monitors the tray and determines if the operator is taking away or replacing the correct part or mandrel in the correct locations. If the operator makes a mistake the system will warn the operator and instruct her on what to correct. A bar code reader 61 senses a bar code 55 on the tray and this information is used to load the correct information regarding the prior inspection steps that have been performed on the given parts in specific tray locations. If in the case as shown here each part is also on a mandrel that contains a data code, the defect review station could read that data code with a sensor at the microscope (57) review to determine the correct mandrel is being handled.

One or more embodiments of the present invention have been described. Nevertheless, it will be understood that various modifications may be made without departing from the spirit and scope of the invention. For example, a different type of converter 46 may be used to convert the machine voltage to the desired output form and this converter may be electrically isolated or non-isolated from the machine voltage. Accordingly, other embodiments are within the scope of the following claims.

What is claimed is:

1. A fixture effective to receive a cylindrical part under test, said cylindrical part having an interior bore extending therethrough, comprising:
   a mandrel having a rod with a diameter effective to be inserted through an interior bore of the cylindrical part and to impart rotational motion to that cylindrical part; and
   a non-transitory, machine-readable, identification code affixed to a portion of said fixture;
   wherein said rod has a base attached to a first end thereof and said identification code is affixed to at least one of said base and said rod; and
   wherein the base mounts with a precise rotational alignment in a receiving fixture.

2. The fixture according to claim 1 wherein the base is rotationally asymmetric and the identification code is affixed to the base.

3. The fixture of claim 1 further comprising an alignment fixture including a v-block which maintains alignment of said rod.

4. The fixture of claim 3 wherein a flexible coupling is disposed between the rod and the base.

5. The fixture of claim 3 wherein a flexible coupling is disposed between the base and a rotational motor.

6. The fixture of claim 1 wherein a sensor is disposed at a location effective to detect the mandrel and a camera is disposed at a location effective to read the identification code and transmit identification data to a database.

7. The fixture of claim 6 wherein an inspection system receives the fixture and the cylindrical part under test and transmits inspection data to the database.

8. The fixture of claim 7 wherein a computer associates said identification data and said inspection data to correlate inspection data to a particular cylindrical part under test.

9. The fixture of claim 8 wherein said identification code is affixed to said fixture in a form selected from the group consisting of a bar code and a radio frequency identification (RFID) tag.

10. The fixture of claim 9 wherein said sensor is selected from the group consisting of a proximity sensor and an optical.

11. An optical inspection system, comprising:
   a. a lens to image an at least partially rotationally symmetric part under inspection;
   b. an electronic camera to capture images projected by said lens;
   c. a rod having a diameter effective to accommodate mounting of said part responsive to its rotational symmetry;
   d. a rotating motor driven mechanical receiving fixture responsively configured to receive said rod and rotate it along an axis perpendicular to optical axis of said lens;
   e. an encoder responsive to said rotating motor for identifying a predetermined rotational alignment of said rod and capturing an image of said part under inspection with said electronic camera upon recognition by said encoder of said predetermined rotational alignment; and
   f. said rod containing an identification code referencing information pertinent to the inspection and processing of said part under inspection.

12. The optical inspection system of claim 11 wherein said optical inspection system contains a sensor responsive to the presence or absence of said rod and an output from said sensor output is used by said optical inspection system to activate reading of said identification code and to assure proper inspection sequence.

13. The optical inspection system of claim 11 wherein said identification code is a lookup to an external database.

14. The optical inspection system of claim 13 wherein said external data base contains information regarding prior manufacturing steps.

15. The optical inspection system of claim 14 wherein said identification code is used to track a single one of a plurality of said at least partially rotationally symmetric part through multiple inspection stations.

16. The optical inspection system of claim 14 wherein said optical inspection system will interact responsively to previously measured and stored operational parameters of said mandrel referenced by said identification code.

17. The optical inspection system of claim 16 wherein said previously measured and stored operational parameters include one or more of rod opacity, correct light levels, a map of surface flaws of said rod, software functionality in said optical inspection system to compensate for said flaws and improve inspection results, use history, calibration records of said optical inspection system to prevent operation given unacceptable use or calibration parameters, and tare weight of the mandrel for use in a weighing station.

18. The optical inspection system of claim 11 wherein said mechanical receiving fixture is responsive to a mechanical transport mechanism that delivers and removes said rod from said mechanical receiving fixture.

19. The optical inspection system of claim 18 wherein said mechanical transport mechanism is a robot.

20. The optical inspection system of claim 15 further including a defect review inspection station responsive to an identification code on a tray of parts where the location of the part in said tray is correlated to a data record containing information pertinent to a prior quality inspection performed by at least one prior inspection system, said defect review inspection station capable of accessing said data record and displaying to an operator images of possible defects taken by said at least one prior inspection system allowing an operator to record a final pass/fail adjudication of possible defects based on review of images of possible defects, wherein a sensor confirms that said operator has correctly removed and replaced from the tray the correct parts per the current review process, said review station effective to alert the operator if there is a mistake in handling.

21. The optical inspection system of claim 15 further including a defect review inspection station responsive to a data code on a part carrier carrying a part previously inspected by at least one prior inspection system, said data code referencing a data record containing information pertinent to a prior quality inspection performed by said at least one prior inspection systems, said defect review inspection station capable of accessing said data record and displaying to an operator images of possible defects taken by said at least one prior inspection system thereby enabling an operator to record a final pass/fail adjudication of possible defects based on review of said images of possible defects.

* * * * *